United States Patent [19]

Silvian

[11] Patent Number: 5,058,581
[45] Date of Patent: Oct. 22, 1991

[54] TELEMETRY APPARATUS AND METHOD FOR IMPLANTABLE TISSUE STIMULATOR

[75] Inventor: Sergiu Silvian, La Crescenta, Calif.

[73] Assignee: Siemens-Pacesetter, Inc., Sylmar, Calif.

[21] Appl. No.: 483,162

[22] Filed: Feb. 20, 1990

[51] Int. Cl.⁵ .............................................. A61N 1/00
[52] U.S. Cl. ............................ 128/419 PG; 128/903; 128/697
[58] Field of Search ............... 128/419 PG, 419 PT, 128/903, 697

[56] References Cited

U.S. PATENT DOCUMENTS

| | | | |
|---|---|---|---|
| 4,223,679 | 9/1980 | Schulman et al. | 128/419 |
| 4,281,664 | 8/1981 | Duggan | 128/696 |
| 4,361,153 | 11/1982 | Slocum et al. | 128/419 |
| 4,453,162 | 6/1984 | Money et al. | 340/870.39 |
| 4,494,545 | 1/1985 | Slocum et al. | 128/419 |
| 4,556,063 | 12/1985 | Thompson et al. | 128/419 |
| 4,658,831 | 4/1987 | Reinhahrd et al. | 128/697 |
| 4,681,111 | 7/1987 | Silvian | 128/419 |
| 4,700,707 | 10/1987 | Batina et al. | 128/419 PT |
| 4,741,340 | 5/1988 | Batina et al. | 128/419 |
| 4,741,341 | 5/1988 | Marach | 128/903 |
| 4,757,816 | 7/1988 | Ryan et al. | 128/419 PT |

Primary Examiner—Francis Jaworski
Assistant Examiner—George Manuel
Attorney, Agent, or Firm—Lisa P. Weinberg; Malcolm J. Romano

[57] ABSTRACT

An improved telemetry system for telemetering digital data from an implantable tissue stimulator such as a heart pacemaker. A carrier signal is pulse modulated in accordance with either or both of stored digital data and a digitized electrocardiogram signal, for coupling onto an electrical lead connected directly to the heart. This arrangement facilitates the transmission of substantially higher data rates than previously could be achieved.

23 Claims, 2 Drawing Sheets

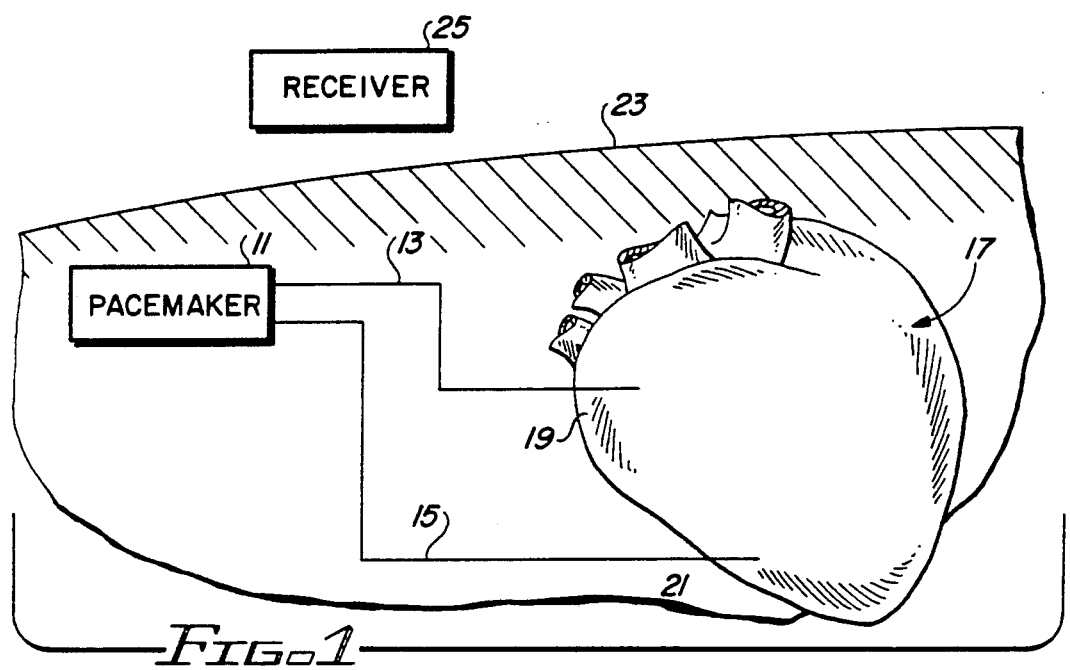
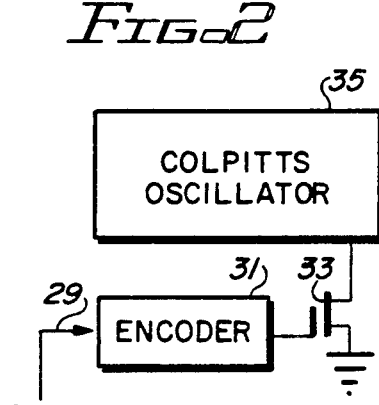
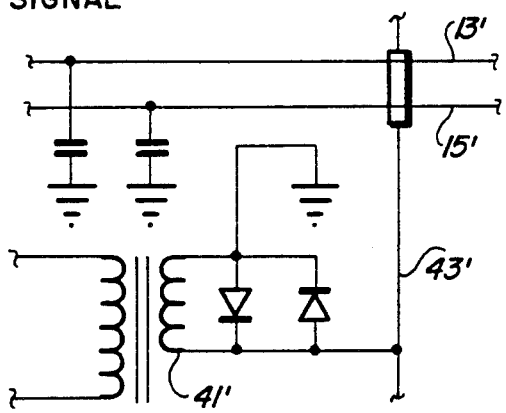
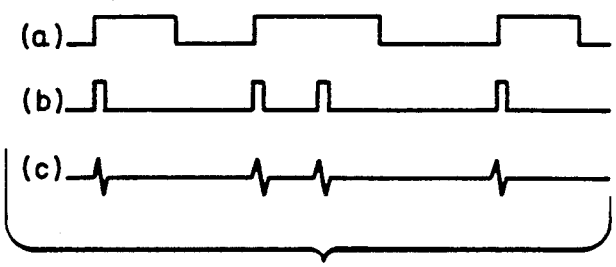

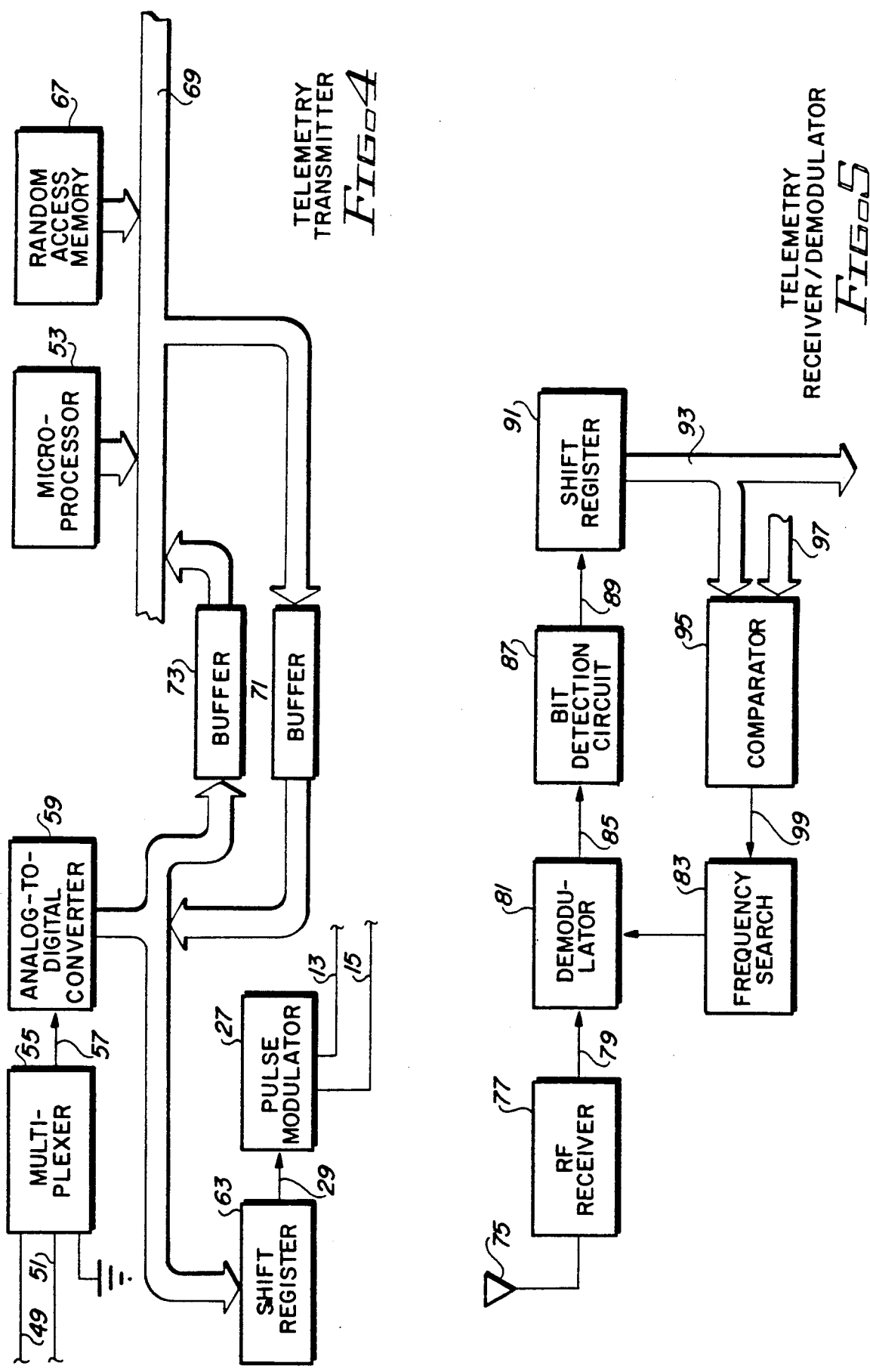

TELEMETRY APPARATUS AND METHOD FOR IMPLANTABLE TISSUE STIMULATOR

BACKGROUND OF THE INVENTION

This invention relates generally to implantable tissue stimulators such as heart pacemakers and, more particularly, to telemetry apparatus and methods for use in transmitting information from such implantable tissue stimulators.

Implantable tissue stimulators of this general kind are becoming increasingly sophisticated, and the need has arisen to transmit, within a reasonable amount of time, increased amounts of data from the stimulator to an external receiver. In the case of a heart pacemaker, for example, it is desired to transmit data representing the real time electrocardiogram (ECG) signal from one or more chambers of the heart, both individually and simultaneously, and in addition to transmit other data accumulated over time in an internal memory. Transmitting all of this data requires a high data rate, on the order of at least about 8,000 bits per second.

Prior telemetry apparatus used in implantable tissue stimulators of this general kind have not been fully adapted to transmit such large amounts of data within a reasonable amount of time. For a multitude of technical reasons, such telemetry apparatus generally have been incapable of transmitting data at the required bit rate.

It should therefore be appreciated that there is a need for an improved telemetry apparatus and related method for transmitting large quantities of data from an implantable tissue simulator such as a heart pacemaker within a reasonable amount of time. The present invention fulfills this need.

SUMMARY OF THE INVENTION

This invention resides in an improved telemetry apparatus and related method for an implantable tissue stimulator such as a heart pacemaker, which is adapted to transmit large amounts of data within a relatively short time duration. The telemetry apparatus includes implantable stimulator means for selectively producing electrical stimulus signals and an electrical lead adapted to carry the stimulus signals to the tissue to be stimulated. Telemetry means are mounted with the stimulator means, for producing a telemetry signal and for transmitting the signal to an external receiver. In accordance with the invention, the telemetry means includes means for coupling the telemetry signal directly onto the electrical lead, which in turn radiates the signal to the receiver. Utilizing the lead in this fashion facilitates transmission at relatively high frequencies, thus facilitating a high data rate.

More particularly, the telemetry means can include digital means for providing a digital telemetry signal along with modulator means for pulse-modulating a carrier signal in accordance with the telemetry signal. The pulse-modulated carrier signal is then coupled onto the electrical lead, for radiating to the receiver.

When the apparatus takes the form of a pacemaker adapted to stimulate a heart muscle, it can further include means for monitoring electrical signals generated by the heart and for producing a corresponding analog electrocardiogram (ECG) signal, and the telemetry means can include analog-to-digital converter means for digitizing the ECG signal to produce the digital telemetry signal. In addition, this digitized ECG signal can be time-division multiplexed with digital data stored in an internal memory device.

In one suitable modulation scheme, the modulator means provides a single burst of the carrier signal when a bit of the telemetry signal has a first state and provides an absence of the carrier signal when a bit has a second state. The burst's duty cycle is preferably less than about 20%, to conserve power. The frequency of the carrier signal is preferably in the range of about 10 to 300 megahertz, and the telemetry signal bit rate is preferably at least about 8000 bits per second.

The tissue stimulator can further include a second electrical lead adapted to carry the stimulus signals to the tissue to be stimulated, and the telemetry means can couple the telemetry signal between the two electrical leads and a metallic case for the implantable means and telemetry means. A dipole antenna can thereby be created, for efficiently radiating the telemetry signal to the receiver.

Other features and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 4 is a simplified block diagram of a telemetry transmitter that is included in the heart pacemaker of FIG. 1.

FIG. 5 is a simplified block diagram of a telemetry receiver/demodulator that is part of the receiver of FIG. 1.

DESCRIPTION OF THE PREFERRED EMBODIMENT

Figure 1:
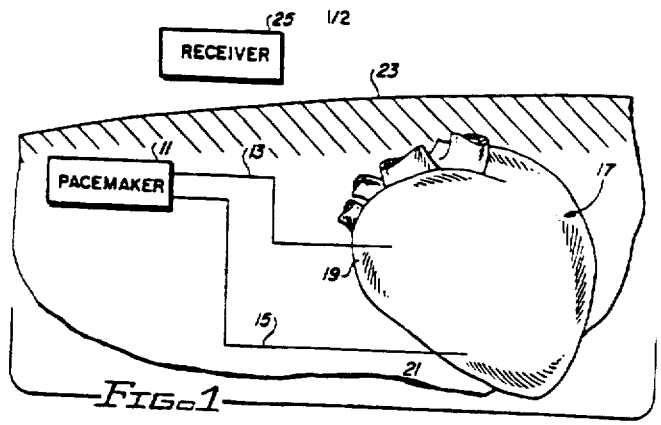
FIG. 1 is a simplified schematic diagram of a heart pacemaker in accordance with a preferred embodiment of the invention, shown implanted in a body and connected via two electrical leads to the body's heart and also shown with a telemetry receiver located exterior to the body.

With reference now to the drawings, and particularly to FIG. 1, there is shown a heart pacemaker 11 adapted to be implanted into a human body and attached via electrical leads 13 and 15 to the body's heart 17. The electrical leads are shown connected to the right auricle 19 and right ventricle 21 of the heart, and they function to carry electrocardiogram (ECG) signals from the heart to the pacemaker, for appropriate analysis, and also to carry stimulus signals from the pacemaker to the heart when a stimulation is determined to be called for.

The pacemaker 11 is adapted to accumulate data relating to its operation, such as the occurrences of detected irregularities in the ECG signals supplied to it and the occurrences of stimulus signals it produces for transmission over the electrical leads 13 and 15 to the heart 17. This data is stored in an internal memory. Periodically, it is desirable to retrieve this stored data from the memory. The pacemaker therefore includes a telemetry subsystem, which modulates a carrier signal in accordance with the stored data and transmits the modulated carrier signal outwardly through the patient's skin 23 to an external receiver 25.

In accordance with the invention, the telemetry signal is used to pulse modulate a 30 megahertz carrier signal, which is then coupled onto one of the electrical leads 13 and 15 for transmission outwardly to the receiver 25. Using the electrical lead as a transmitting antenna enables the pacemaker to transmit significantly more data than was previously possible. In addition, because of the modulated carrier signal's frequency is relatively high, the telemetry transmission will not interfere with the pacemaker's ongoing monitoring of the ECG signals it receives on the same lead.

Figure 2:
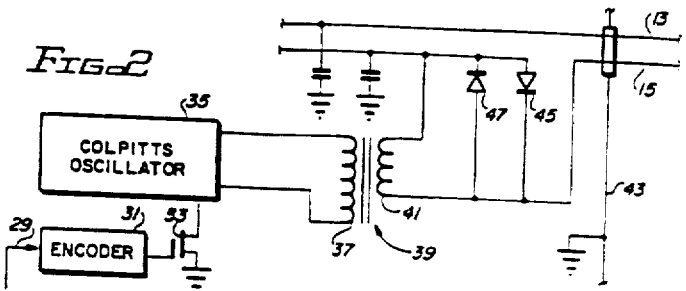
FIG. 2 is a simplified block diagram of a telemetry modulator that is part of the heart pacemaker of FIG. 1.
Figure 3:
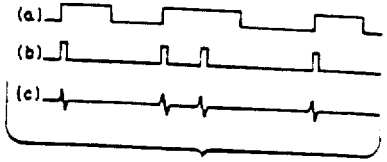
FIG. 3 is a timing diagram depicting several waveforms present in the telemetry modulator of FIG. 2.

FIG. 2 depicts a telemetry pulse modulator for modulating the carrier signal with the digital telemetry signal and for coupling the modulated signal onto the electrical lead 15. The telemetry signal, which has a non-return-to-zero (NRZ) format and a bit rate of about 8,192 hertz, is supplied on line 29 to an encoder 31. The encoder converts the NRZ-format signal into a corresponding digital pulse signal, in which each "one" bit of the NRZ signal becomes a short pulse and each "zero" bit of the NRZ signal becomes no pulse at all. The NRZ signal and the resulting pulse signal are depicted in FIGS. 3(a) and (b), respectively. The pulses of the pulse signal preferably have a duty cycle of about one-eighth. The pulse signal is used to switch on and off a field-effect transistor 33, which enables and disables a conventional Colpitts oscillator 35, and thereby produces corresponding bursts having a frequency of about 30 megahertz. These bursts are depicted in FIG. 3(c).

The 30 megahertz bursts from the Colpitts oscillator 35 are supplied to the input winding 37 of a step-down transformer 39. The transformer's low-impedance output winding 41 is connected in series with the electrical lead 15, which thereby functions as an antenna for transmitting the information outwardly to the receiver 25 (FIG. 1). The pacemaker's metallic case 43 is connected to signal ground, to provide a return path for the transmitted signal. Data is thereby efficiently transmitted to the receiver. Back-to-back diodes 45 and 47 are connected in parallel with the transformer's secondary winding 41 to prevent an excessive voltage from being coupled back to the oscillator 35 if and when the heart 17 (FIG. 1) ever is defibrillated.

Using the encoding scheme described above sharply reduces the amount of power required to telemeter the stored data. Since bursts of the 30 megahertz carrier signal occur only for "one" bits, and not for "zero" bits, and since each such burst has a duty cycle of only about one-eighth, the oscillator 35 operates on average only about one-sixteenth of the time. When the bursts are not being generated, no power is being consumed. Using this encoding scheme, an average current drain of only 5 to 15 microamps can be achieved.

Figure 2A:
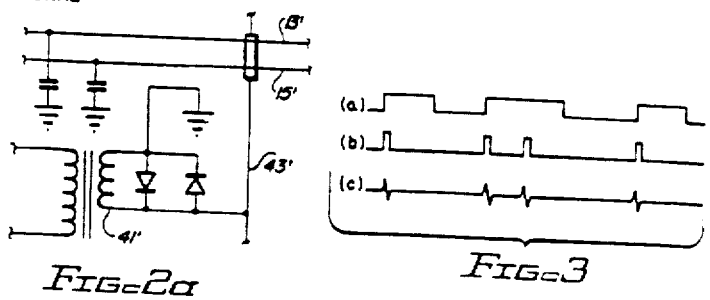
FIG. 2(a) is a simplified schematic diagram of alternative circuitry to the circuitry to FIG. 2, for coupling the telemetry signal onto the electrical leads.

An alternative circuit for coupling the modulated carrier signal onto electrical leads 13' and 15' and case 43' is depicted in FIG. 2(a). In this alternative circuit, the case is connected not to signal ground, but rather to one terminal of the transformer's secondary winding 41'. The secondary winding's other terminal is connected to signal ground. This alternative circuit configuration is preferred, because it allows both leads to be at the same rf voltage, with improved radiation. A dipole antenna is thereby realized.

As described above, the pacemaker's telemetry subsystem can in one mode be used to transmit outwardly to the receiver 25 data that has been accumulated in an internal memory. At the specified bit rate of 8,192 bits per second, substantial amounts of data can be transmitted within a very short time duration. This large capacity makes possible the transmission not only of stored data, but also of real-time data representing the digitized ECG signal. Circuitry for formatting and transmitting this data is depicted in FIG. 4.

In FIG. 4, two analog ECG signals are received on lines 49 and 51. One signal represents the ECG signal from the heart's right auricle 19 and the other represents the ECG signal from the heart's right ventricle 21 (see FIG. 1). Under the control of a microprocessor 53, a multiplexer 55 selects one of the two ECG signals and couples it via line 57 to an analog-to-digital (A/D) converter 59. A CMOS switched capacitor A/D converter is preferably used, because it draws very low current and is compatible with the selected bit rate.

The resulting 8-bit digital word sequence is transmitted in parallel format on a data bus 61 from the A/D converter 59 to an 8-bit shift register 63, which in turn serializes the data for transmission on line 29 to the pulse modulator 27. This pulse modulator was described in detail above with reference to FIG. 2. As described above, the pulse modulator provides bursts of the 30 megahertz carrier signal in accordance with the digital data, for transmission from the electrical lead 15 (in the FIG. 2 embodiment) or leads 13 and 15 (in the FIG. 2(a) embodiment) to the external receiver 25.

Alternatively, when operating in the mode described earlier of transmitting only stored data, 8-bit words are retrieved successively from a random-access memory (RAM) 67 and placed on an 8-bit data bus 69. From there, the successive words are connected via a buffer 71 to the same 8-bit data bus 61 that in the other mode carries the digitized ECG signals and, in turn, through the 8-bit shift register 63 to the pulse modulator 27.

In an another operating mode, it is desirable to transmit both real-time digitized ECG signals, as well as previously-stored data, in a time-division multiplexed format. This is accomplished, again under the control of the microprocessor 53, by conditioning the multiplexer 55 to select first one ECG signal then the other for digitizing by the A/D converter 59, after which one 8-bit word is read from the RAM 67. The data are alternatively placed on the data bus 61 for passage through the shift register 63 to the pulse modulator 27. This multiplexing process is repeated for as long as desired.

Portions of this same telemetry transmitter of FIG. 4 can be used to digitize and store data in the RAM 67 when data is not being telemetered. In particular, such data can be selected by the multiplexer 55 and one or more submultiplexers (not shown), for transmission on line 57 to the A/D converter 59, which in turn produces a succession of corresponding 8-bit words for output on the data bus 61. These words are coupled through a buffer 73 onto the data bus 69, for loading into the RAM 67, all under the control of the microprocessor 53. Eventually, this same data that is being stored can be selected for telemetry to the receiver 25, as described above.

As previously discussed, the modulation scheme implemented by the pulse modulator 27 provides a burst of the 30 megahertz carrier signal only when a "one" bit is being transmitted. No signal is transmitted when a "zero" bit is present. Accordingly, to prevent the possibility of no bursts being transmitted for an extended time duration, which could lead to a loss of synchronization in the receiver 25, an 8-bit word of all "zero's" is not allowed. This is not a significant drawback, because 255 8-bit words still remain usable.

The receiver 25 for receiving, demodulating and detecting the data transmitted from the pacemaker 11 is depicted in FIG. 5. It includes an antenna 75 and rf receiver 77 tuned approximately to the 30 megahertz carrier signal. The rf receiver supplies the received signal on line 79 to a demodulator 81. The demodulator preferably has both automatic gain control and automatic frequency control, with the latter being accomplished using an automatically tunable local oscillator. The local oscillator's tuning range must be adequate to track the frequency deviations that might occur in the Colpitts oscillator 35 of the pacemaker's pulse modulator 27.

To enable the demodulator 81 to achieve an initial frequency lock with the received carrier signal, a frequency search circuit 83 supplies a saw-tooth waveform on line 85 to the demodulator 81. The demodulator uses this saw-tooth waveform to control the frequency of its local oscillator. At some point in the range of the saw-tooth waveform, the demodulator frequency will reach the same frequency as the incoming carrier signal, and the carrier signal will at that time be properly demodulated.

The demodulator 81 outputs a digital data stream corresponding to that depicted in FIG. 3(b) when properly locked onto the received carrier signal. This digital signal is transmitted on line 85 to a bit detection circuit 87, which includes a threshold detector having a threshold automatically selected to be approximately one-half of the signal's peak value. The bit detection circuit also includes a conventional clock recovery circuit, to facilitate detection of the individual bits. The resulting detected data, in NRZ form, is then transmitted on line 89 to the data input terminal of a shift register 91, which accumulates each succession of 8-bit words. The 8-bit words are output in parallel on a data bus 93, for further processing.

Synchronization is achieved by continuously monitoring the 8-bits currently being stored in the shift register 91. Thus, an 8-bit comparator 95 continuously compares the 8-bit words present on the data bus 93 with a stored 8-bit code supplied on lines 97. When the two 8-bit words are in agreement, a lock signal is output on line 99, to terminate further frequency scanning by the demodulator and to inform other subsystems (not shown) in the receiver 25 that synchronization has been reached.

It should be appreciated from the foregoing description that the present invention provides an improved telemetry system for telemetering substantially increased amounts of data from a heart pacemaker. A carrier signal is pulse modulated in accordance with either or both of stored digital data and a digitized electrocardiogram signal, for coupling onto an electrical lead connected directly to the heart. This arrangement facilitates the transmission of substantially higher data rates than previously could be achieved.

Although the invention has been described in detail with reference only to the presently preferred embodiment, those skilled in the art will appreciate that various modifications can be made without departing from the invention. Accordingly, the invention is only defined only by the following claims.

What is claimed is:

1. A living tissue stimulator apparatus comprising:
    implantable stimulator means for selectively producing electrical stimulus signals;
    an electrical lead adapted to carry the stimulus signals from the stimulator means to the tissue;
    telemetry means mounted with implantable means for producing a telemetry signal and for transmitting it therefrom; and
    external receiver means for receiving the telemetry signal transmitted by the telemetry means;
    wherein the telemetry means includes means for coupling the telemetry signal onto the electrical lead, for radiation outwardly to the receiver means.

2. A living tissue stimulator apparatus as defined in claim 1, wherein:
    the apparatus further includes
        a metallic case for housing the implantable stimulator means and telemetry means, and
        a second electrical lead adapted to carry the stimulus signals from the simulator means to the tissue to be stimulated; and
    the telemetry means includes means for applying the telemetry signal between the two electrical leads and the case, the provide a dipole antenna.

3. A living tissue stimulator apparatus as defined in claim 1, wherein the telemetry means includes:
    digital means for providing a digital telemetry signal; and
    modulator means for pulse-modulating a carrier signal with the digital telemetry signal, for coupling onto the electrical lead and radiation outwardly to the receiver means.

4. A living tissue stimulator apparatus as defined in claim 3, wherein:
    the living tissue to be stimulated is heart muscle tissue;
    the apparatus is a pacemaker adapted to stimulate the heart muscle tissue;
    the apparatus further includes means for monitoring electrical signals generated by the heart and for producing a corresponding analog electrocardiogram signal; and
    the telemetry means includes analog-to-digital converter means for digitizing the analog electrocardiogram signal to produce a digitized electrocardiogram signal.

5. A living tissue stimulator apparatus as defined in claim 4, wherein the telemetry means further includes:
    memory means for storing digital data; and
    multiplexing means for multiplexing the digital data stored by the memory means with the digitized electrocardiogram signal provided by the analog-to-digital converter means, to produce the digital telemetry signal.

6. A living tissue stimulator apparatus as defined in claim 3, wherein:
    the digital telemetry signal includes a succession of bits, each having either a first state or a second state; and
    the modulator means includes means for providing a single burst of the carrier signal when a bit of the telemetry signal has the first state and an absence of the carrier signal when a bit has the second state.

7. A living tissue stimulator apparatus as defined in claim 6, wherein:
    the single burst of the carrier signal, provided by the modulator means when a bit of the telemetry signal has the first state has a duty cycle of less than about 0.2; and the carrier signal modulated by the telemetry means has a frequency in the range of 10 to 300 megahertz.

8. A living tissue stimulator apparatus comprising:
implantable stimulator means for selectively producing electrical stimulus signals for transmission to living tissue;
an electrical lead adapted to carry the stimulus signals from the implantable stimulator means to the tissue;
telemetry means mounted with the stimulator means for producing a telemetry signal and for transmitting the telemetry signal therefrom, the telemetry means including
digital means for producing a digital telemetry signal,
modulator means for pulse modulating a carrier signal with the digital telemetry signal,
transmitter means for transmitting the pulse-modulated carrier signal therefrom, and
means for coupling the pulse-modulated carrier signal onto the electrical lead, for radiation outwardly to external receiver means; and
the external receiving means adapted to receive the pulse-modulated carrier signal transmitted by the coupling means.

9. A living tissue stimulator apparatus as defined in claim 8, wherein:
the apparatus further includes
a metallic case for housing the implantable stimulator means and telemetry means, and
a second electrical lead adapted to carry the stimulus signals from the stimulator means to the tissue; and
the telemetry means includes means for applying the telemetry signal between the two electrical leads and the case, to provide a dipole antenna.

10. A living tissue stimulator apparatus as defined in claim 8, wherein:
the apparatus is a pacemaker and the tissue is a heart muscle;
the apparatus further includes means for monitoring electrical signals generated by the heart muscle and for producing a corresponding analog electrocardiogram signal;
the telemetry means includes analog-to-digital converter means for digitizing the analog electrocardiogram signal to produce the digital telemetry signal.

11. A living tissue stimulator apparatus as defined in claim 10, wherein the telemetry means further includes:
memory means for storing digital data; and
multiplexing means for multiplexing the digital data stored by the memory means with the digitized electrocardiogram signal provided by the analog-to-digital converter means to produce the digital telemetry signal.

12. A living tissue stimulator apparatus as defined in claim 10, wherein:
the carrier signal modulated by the telemetry means has a frequency in the range of 10 to 300 megahertz.

13. A living tissue stimulator apparatus comprising:
implantable stimulator means for selectively producing electrical stimulus signals for transmission to the tissue;
telemetry means mounted with the stimulator means for producing a telemetry signal and for transmitting the telemetry signal therefrom, the telemetry means including
digital means for producing a digital telemetry signal, wherein the digital telemetry signal includes a succession of bits, each having either a first state or a second state;
modulator means for pulse modulating a carrier signal with the digital telemetry signal, the modulator means having means for providing a single burst of the carrier signal when a bit of the telemetry signal has the first state and an absence of the carrier signal when a bit has the second state; and
transmitter means for transmitting the pulse-modulated carrier signal therefrom.

14. A living tissue stimulator apparatus as defined in claim 13, wherein:
the single burst of the carrier signal, provided by the modulator means when a bit of the telemetry signal has the first state, has a duty cycle of less than about 0.2; and
the carrier signal modulated by the telemetry means has a frequency in the range of 10 to 300 megahertz.

15. A method of telemetering data from an implanted tissue stimulator to an external receiver, wherein the tissue stimulator includes means for selectively producing electrical stimulus signals and an electrical lead for carrying the stimulus signals to the tissue, comprising a step of:
coupling a telemetry signal onto the electrical lead, for radiation outwardly to the external receiver.

16. A method as defined in claim 15 wherein:
the implanted tissue stimulator further includes a metallic case and a second electrical lead for carrying the stimulus signals to the tissue; and
the method further includes a step of applying the telemetry signal between the two electrical leads and the case, such that a dipole antenna configuration is provided.

17. A method of telemetering data from an implanted tissue stimulator to an external receiver, wherein the tissue stimulator includes means for selectively producing electrical stimulus signals and an electrical lead for carrying the stimulus signals to the tissue to be stimulated, comprising the steps of:
producing a digital telemetry signal;
pulse modulating a carrier signal with the digital telemetry signal; and
transmitting the pulse-modulated carrier signal to the external receiver by coupling the pulse-modulated carrier signal onto the electrical lead.

18. A method as defined in claim 17, wherein:
the implanted tissue stimulator is a pacemaker adapted to stimulate the heart muscle;
the method further includes steps of monitoring electrical signals generated by the heart and producing a corresponding analog electrocardiogram signal; and
the step of producing includes a step of digitizing the analog electrocardiogram signal to produce the digital telemetry signal.

19. A method as defined in claim 18, wherein the step of producing further includes steps of:
storing digital data; and
multiplexing the stored digital data with the digitized electrocardiogram signal to produce the digital telemetry signal.

20. A method as defined in claim 17, wherein:

the digital telemetry signal includes a succession of bits, each having either a first state or a second state; and the step of modulating includes a step of providing a single burst of the carrier signal when a bit of the telemetry signal has the first state and an absence of the carrier signal when a bit has the second state.

21. A method as defined in claim 20, wherein:

the single burst of the carrier signal provided in the step of modulating has a duty cycle of less than about 0.2; and the carrier signal modulated in the step of modulating has a frequency in the range of 10 to 300 megahertz.

22. A pacemaker for stimulating a heart comprising:

implantable stimulator means for selectively producing electrical stimulus signals;

first and second electrical leads adapted to carry the stimulus signals from the stimulator means to the heart;

means for monitoring electrical signals generated by the heart and for producing a corresponding analog electrocardiogram signal;

analog-to-digital converter means for digitizing the analog electrocardiogram signal to produce a digitized electrocardiogram signal;

memory means of storing digital data;

multiplexing means for multiplexing the digital data stored by the memory means with the digitized electrocardiogram signal provided by the analog-to-digital converter means, to produce a digital telemetry signal;

modulator means for pulse-modulating a carrier signal with the digital telemetry signal;

a metallic case for housing the implantable stimulator means, the means for monitoring, the analog-to-digital converter means, the memory means, the multiplexing means and the modulator means; and means for applying the pulse-modulated carrier signal between the first and second electrical leads and the case, to provide a dipole antenna for radiating the carrier signal outwardly.

23. A heart pacemaker as defined in claim 22 wherein:

the digital telemetry signal includes a succession of bits, having either a first state or a second state;

the modulator means includes means for providing a single burst of the carrier signal when a bit of the telemetry signal has the first state and an absence of the carrier signal when a bit has the second state;

the single burst of the carrier signal, provided by the modulator means when a bit of the telemetry signal has the first state, has a duty cycle of less than about 0.2; and the carrier signal modulated by the modulator means has a frequency in the range of 10 to 300 megahertz.

* * * * *

UNITED STATES PATENT AND TRADEMARK OFFICE
CERTIFICATE OF CORRECTION

PATENT NO. : 5,058,581
DATED : Oct. 22, 1991
INVENTOR(S) : Sergiu Silvian

It is certified that error appears in the above-identified patent and that said Letters Patent is hereby corrected as shown below:

Sheet 1, Fig. 2 (Formal Drawings), please delete symbol for diode 45. The side of the inductor 41, previously connected to the cathode of diode 45, should be redrawn to connect to the cathode of diode 47.

Sheet 1, Fig. 2 (Formal drawings), please add a symbol for a diode, designated as --45-- in parallel with diode 47, so that the anode of diode 45 is connected to the cathode of diode 47 and the cathode of diode 45 is connected to the anode of diode 47.

Sheet 1, Fig. 2 (Formal drawings), please delete the short which appears across diode 47.

Signed and Sealed this

Twelfth Day of July, 1994

Attest:

BRUCE LEHMAN

Attesting Officer

Commissioner of Patents and Trademarks